(12) United States Patent
Kajihara et al.

(10) Patent No.: US 9,127,041 B2
(45) Date of Patent: Sep. 8, 2015

(54) PROCESS FOR PRODUCTION OF PEPTIDE THIOESTER

(71) Applicant: Glytech, Inc., Kyoto (JP)

(72) Inventors: Yasuhiro Kajihara, Osaka (JP); Ryo Okamoto, Osaka (JP); Izumi Sakamoto, Tokushima (JP); Kazuyuki Ishii, Tokyo (JP)

(73) Assignee: Glytech, Inc., Kyoto (JP)

( * ) Notice: Subject to any disclaimer, the term of this patent is extended or adjusted under 35 U.S.C. 154(b) by 0 days.

(21) Appl. No.: 14/162,642

(22) Filed: Jan. 23, 2014

(65) Prior Publication Data

US 2014/0249294 A1    Sep. 4, 2014

Related U.S. Application Data

(62) Division of application No. 13/379,832, filed as application No. PCT/JP2010/060443 on Jun. 21, 2010, now Pat. No. 8,642,725.

(30) Foreign Application Priority Data

Jun. 26, 2009    (JP) ................................. 2009-151713

(51) Int. Cl.
| | | |
|---|---|---|
| *A61K 38/00* | (2006.01) | |
| *C07K 2/00* | (2006.01) | |
| *C07K 4/00* | (2006.01) | |
| *C07K 5/00* | (2006.01) | |
| *C07K 7/00* | (2006.01) | |
| *C07K 14/00* | (2006.01) | |
| *C07K 16/00* | (2006.01) | |
| *C07K 17/00* | (2006.01) | |
| *C07K 1/107* | (2006.01) | |

(52) U.S. Cl.
CPC ............ *C07K 1/1077* (2013.01); *C07K 1/1072* (2013.01)

(58) Field of Classification Search
CPC ............ C07K 2319/00; C07K 1/1077; C07K 2319/21; C07K 2319/23; C07K 14/001; C07K 2319/41; C07K 2319/42; C07K 1/13
See application file for complete search history.

(56) References Cited

U.S. PATENT DOCUMENTS 2,539,483 A    1/1951 Ruskin

FOREIGN PATENT DOCUMENTS

| EP | 2000474 A1 | 12/2008 |
|---|---|---|
| FR | 1454653 A | 2/1966 |
| NL | 6513990 A | 1/1966 |
| WO | 96/34878 A1 | 11/1996 |
| WO | 2007/043615 A1 | 4/2007 |
| WO | 2007/114454 A1 | 10/2007 |
| WO | 2009/042668 A2 | 4/2009 |

OTHER PUBLICATIONS

Hoffman, Eliahu, et al., "Acylguanidines as intermediates in peptide synthesis"; Canadian Journal of Chemistry, vol. 43; Jan. 1, 1965; XP055120318; pp. 3103-3105 (3 pages).
EPO Communication and Extended European Search Report dated Jun. 4, 2014, issued by the European Patent Office in corresponding European Patent Application No. 10792048.0 (9 pages).
Second Office Action issued May 13, 2014, by the State Intellectual Property Office of the People's Republic of China in corresponding Chinese Patent Application No. 201080028424.9, with English translation (14 pages).
Yuan, Ma, et al., "Peptide Segments Ligation and Synthesis of Peptide Thioester and Peptide Aldehyde"; Progress in Chemistry, vol. 15, No. 5; Sep. 2003; pp. 393-400 (9 pages).
Clave, Guillaume, et al., "A novel heterotrifunctional peptide-based cross-linking reagent for facile access to bioconjugates. Applications to peptide fluorescent labelling and immobilisation"; Organic & Biomolecular Chemistry, Journal of The Royal Society of Chemistry, vol. 6, No. 17; Jan. 1, 2008; XP55035016, ISSN: 1477-0520, DOI: 10.1039/b807263a; pp. 3065-3078 (14 pages).
Beligere, Gangamani S., et al., "Conformationally Assisted Protein Ligatin Using C-Terminal Thioester Peptides"; Journal of the American Chemical Society, vol. 121, No. 26, 1999; pp. 6332-6333. [NOTE: This reference was cited by the Examiner in U.S. Appl. No. 13/379,832, in the Restriction Requirement issued Jul. 3, 2013.].
International Search Report w/translation from PCT/JP2010/060443 dated Sep. 14, 2010 (2 pages).
J. Brask, et al.; "Fmoc Solid-Phase Synthesis of Peptide Thiesters by Masking as Trithioortho"; American Shemical Society, 2003; vol. 5, No. 16, pp. 2951-2953 (3 pages).
E.C.B. Johnson et al.; "Insights into the Mechanism and Catalysis of the Native Chemical Ligation Reaction", J. Am. Chem. Soc.; 2006, vol. 128, No. 20, p. 6640-6646 (7 pages).
R. Okamoto et al.; "Efficient Substitution Reaction from Cysteine to the Serine Residue of Glycosylated Polypeptide: Repetitive Peptide Segment Ligation Strategy and the Synthesis of Glycosylated Tetracontapeptide Having Acid Labile Sialyl-TN Antigens"; J. Org. Chem. 2009; vol. 74, No. 6, pp. 2494-2501 (8 pages).
R. Ingenito, et al.; "Solid Phase Synthesis of Peptide C-Terminal Thioesters by Fmoc/t-Bu Chemisty"; J. Am. Chem. Soc. 1999; 121, pp. 11369-11374 (6 pages).
E.C. Schwartz et al.; "The splice is right': how protein splicing is opening new doors in protein science"; The Royal Society of Chemistry Journal, 2003; pp. 2087-2090 (4 pages).

(Continued)

*Primary Examiner* — Marcela M Cordero Garcia
*Assistant Examiner* — Kaipeen Yang
(74) *Attorney, Agent, or Firm* — Osha Liang LLP

(57) ABSTRACT

A process for chemically converting a peptide chain into a peptide thioester includes, when a —C(=X)—$R_1$ group is introduced to the thiol group of the cysteine residue and then the resulting peptide is reacted with a compound having a leaving group represented by the formula: —NH—C(=Y)NH$R_3$ in an organic solvent, the —NH—C(=Y)NH$R_3$ group binds via addition reaction to the carboxyl group of the N-terminal-side peptide bond of the cysteine residue, whereby the peptide bond is cleaved and the C-terminal-side peptide fragment is cut off. Further, when the resulting peptide chain having the —NH—C(=Y)NH$R_3$ group is reacted with a thiol in a buffer solution, a thiol exchange reaction occurs, namely, the thiol group of the thiol binds to the carbonyl carbon to which the —NH—C(=Y)NH$R_3$ group has bound, whereby the —NH—C(=Y)NH$R_3$ group is eliminated.

20 Claims, No Drawings

(56) References Cited

OTHER PUBLICATIONS

W. Muir; "Semisynthesis of Proteins by Expressed Protein Ligation"; Annu. Rev. Biochem. 2003; 72:249-289 (43 pages).

G. R. Stark; "Cleavage at Cysteine after Cyanylation"; Methods in Enzymology, vol. 47, 1977; pp. 129-132 (4 pages).

S. Nakagawa et al.; "Chemical Cleavage of Recombinant Fusion Proeins to Yield Peptide Amides"; J. Am. Chem. Soc., 1994, 116(12); pp. 5513-5514 (2 pages).

R. Sola et al.; "A New Type of Safety-catch Linker cleaved by Intramolecular Activation of an Amide Anchorage and allowing Aqueous Processing in Solid-phase Peptide Synthesis"; J. Chem. Soc., Chem. Commun., 1993; pp. 1786-1788 (3 pages).

R. Pascal et al.; "Carboxyl-protecting Groups Convertible into Activating Groups. Carbamates of o-Aminoanilides are Precursors of Reactive N-Acylureas"; Tetrahedron Letters, vol. 35, No. 34, 1994; pp. 6291-6294 (4 pages).

Official Action issued Sep. 2, 2014, by the Japan Patent Office in corresponding Japanese Patent Application No. JP2011-519878, with Google machine translation (6 pages).

Dawson, Phillip E., et al., "Synthesis of Proteins by Native Chemical Ligation"; Science, vol. 266, Nov. 4, 1994; pp. 776-779.

PROCESS FOR PRODUCTION OF PEPTIDE THIOESTER

CROSS REFERENCE TO RELATED APPLICATIONS

This application is a Divisional Application of the Non-provisional Application No. 13/379,832, filed on Dec. 21, 2011, which is a national stage application of PCT/JP2010/060443 filed on Jun. 21, 2010, which claims priority to Japanese Application No. 2009-151713, filed on Jun. 26, 2009. The present application claims priorities to all these prior applications and incorporates these prior applications by reference in their entirety.

TECHNICAL FIELD

The present invention relates to a process for production of a peptide thioester.

BACKGROUND ART

Various methods such as biosynthesis, chemical synthesis and cell-free synthesis are known to be used for synthesizing proteins. In the biosynthesis method, a protein is obtained by utilizing the inside of a cell such as an *Escherichia coli* cell and introducing and expressing DNA encoding the protein to be synthesized in the cell. In the chemical synthesis, the objective protein is synthesized by sequentially binding amino acids in an organochemical manner. In the cell-free synthesis, the protein is synthesized in a cell-free system utilizing an enzyme, etc., present in various cells such as the *Escherichia coli* cell. These methods are appropriately used separately or combined depending on the intended use, the size and the nature to be added, of the protein.

At present, in order to synthesize a protein homogeneously having a particular modification with a sugar chain or a lipid, etc., in a middle part of its amino acid sequence, amino acids are modified with the sugar chain or the lipid, etc., in advance and then a peptide chain including the modified amino acids is chemically synthesized.

A solid-phase synthesis is mainly used as the method for chemically synthesizing the peptide chain. However, the peptide chain obtained by the solid-phase synthesis is generally a short chain, and is composed of at longest about 50 residues.

Thus, the short peptide chains are separately prepared and then they are ligated in order to synthesize the long peptide chain having the modification. Various techniques for ligating the peptide chains have been reported, and one widely used technique is the native chemical ligation method (NCL method). The NCL method can also be applied between unprotected peptide chains, and is known to be useful for forming a native amide bond (peptide bond) at a ligation site (e.g., Patent Literature 1). The NCL method is a chemoselective reaction between a first peptide having an α-carboxythioester moiety at its C-terminal and a second peptide having a cysteine residue at its N-terminal, and a thiol group (SH group, also referred to as a sulfhydryl group) of the cysteine side chain is selectively reacted with carbonyl carbon of a thioester group, whereby a thioester binding initial intermediate is formed by the thiol exchange reaction. This intermediate spontaneously performs intramolecular transposition to give the native amide bond at the ligation site while it regenerates the cysteine side chain thiol.

In this method, two peptide chains can be ligated via the peptide bond only by mixing the unprotected peptides in a buffer solution. In the NCL method, even when compounds such as peptides having many functional groups are reacted, the C-terminal of one peptide can be ligated selectively to the N-terminal of the other peptide. From these points, it is important to determine in what way to utilize the NCL method in order to chemically synthesize the protein.

However, a problem when the NCL method is utilized includes the preparation of a peptide thioester having an α-carboxythioester moiety at its C-terminal, which is required as a raw material. Various methods have been reported for preparing the peptide thioester, and those methods can be generally classified into two types based on the solid-phase synthesis.

A first one is the method of constructing the peptide thioester on a resin. In this method, the peptide thioester can be obtained together with cleavage of the peptide chain from the resin after constructing the peptide (e.g., Boc solid-phase synthesis, Fmoc solid-phase synthesis). A second one is the method of constructing the peptide chain on the solid phase via a linker equivalent to thioester (Safety catch linker, Fujii method, Dawson method, Mercapto propanol method, Kawakami method, Danishefsky method, Hojo method, Aimoto method, etc.). In this method, thioester is obtained by activating the peptide chain C-terminal constructed by appropriately treating with the linker, followed by thiolysis of the peptide chain (Non-patent Literature 1).

In addition to these methods, the method in which a protected peptide so that the side chain is protected by the solid-phase synthesis and only the carboxyl group at the C-terminal is free is synthesized followed by thioesterification under an appropriate condensation condition has also been reported (e.g., Patent Literature 2). Any of these methods have been well-established, and used for various protein syntheses. However, the size of the peptide thioester capable of being synthesized is limited because these methods are limited to restrictions of the solid-phase synthesis. Further, in the method using the linker, a non-native amino acid derivative or a specific derivative must be chemically synthesized separately. Thus, their procedures cannot always be said to be simple.

An intein method solved the restriction of the thioesterification by the solid-phase synthesis (Non-patent Literature 2). In this method, a polypeptide fragment biosynthesized from a cell can be obtained as thioester. In the intein method, the peptide chain is thioesterified by utilizing a protein splicing function that occurs in the particular protein sequence, and the polypeptide chain is obtained as thioester. An advantage of this method is that a long chain peptide thioester can be obtained. The synthesis of the large modified protein, which had been considered to be difficult to synthesize until now, has become possible by combining this method with the chemical synthesis method (Non-patent Literature 3). The method of expressing the polypeptide chain and obtaining it has been studied extensively, and well-established as a basic technique in biology.

However, when the intein method is used, a peptide sequence to be targeted is necessary and an expressed intein complex protein must be folded to take on an inherent three-dimensional structure because not only is the polypeptide expressed but also the protein splicing is caused to function. Thus, depending on the polypeptide sequence to be expressed, the peptide thioester is not always obtained in association with sufficient conditions for optimization and the accompanying complications in the work.

Meanwhile, the method of cleaving the peptide chain at a position of a cysteine residue by reacting a compound with the SH group of the cysteine residue in the peptide (Non-patent Literatures 4 and 5), and the method of cleaving the peptide bound to the solid phase using the linker (Non-patent Literatures 6 and 7) are known as the methods of cleaving the peptide. Also, the method of cleaving the peptide bond on the C-terminal-side of a methionine residue using cyanogen bromide (CNBr) is known. However, these are not methods for obtaining a peptide fragment as the thioester.

RELATED ART LITERATURE

Patent Literature

Patent Literature 1: International Publication WO 96/34878
Patent Literature 2: International Publication WO 2007/114454

Non-patent Literature

Non-patent Literature 1: Ingenito et al., J. Am. Chem. Soc., 121: 11369-11374, 1999.
Non-patent Literature 2: Schwartz et al., CHEM COMMUN., 2087-2090, 2003.
Non-patent Literature 3: Muir, Annu. Rev. Biochem., 72: 249-289, 2003.
Non-patent Literature 4: Stark G R, Methods of Enzymology, 47: 129-132, 1977.
Non-patent Literature 5: Nakagawa et al., J. Am. Chem. Soc., 116: 5513-5514, 1994.
Non-patent Literature 6: Sola et al., J. Chem. Soc. Chem. Commun., 1786-1788, 1993.
Non-patent Literature 7: Pascal et al., Tetrahedron Letters, Vol. 35, No. 34: 6291-6294, 1994.

SUMMARY OF INVENTION

Problem to be Solved by the Invention

In the peptide thioesterification shown in the above background art, the peptide capable of being thioesterified is limited to the peptide chain synthesized in the solid phase and the peptide chain to be targeted by the protein splicing. This is because any of these methods require the non-native amino acid derivative, the linker and the particular three-dimensional structure, etc.

Thus, it is an object of the present invention to provide a novel process for chemically converting a polypeptide chain into a peptide thioester.

Means for Solving Problems

The present inventors considered that a process for selectively activating a peptide C-terminal by targeting a native amino acid residue in a peptide sequence is required. In such a process, the peptide chain in any peptide obtained by any method such as biosynthesis can be selectively activated and thioesterified.

Thus, the present inventors focused on a cysteine residue that is a special sulfur-containing amino acid among the native amino acids. And the present inventors have found that as shown in the following figure, a —C(=X)—$R_1$ group is introduced into a thiol group of the cysteine residue, and a compound having a leaving group represented by —NH—C(=Y)$NHR_3$ is reacted therewith in an organic solvent to add the —NH—C(=Y)$NHR_3$ group to a carboxyl group of a peptide bond on an N-terminal-side of the cysteine residue, whereby the peptide bond is cleaved and a peptide fragment on a C-terminal-side is cut off. Further, the present inventors have found that the resulting peptide chain can be converted into a peptide thioester by an exchange reaction with thiol in which a thiol compound is reacted with the peptide chain to which the —NH—C(=Y)$NHR_3$ group has been added in a buffer solution, thereby allowing the thiol group of the thiol compound to be bound to carbonyl carbon to which the —NH—C(=Y)$NHR_3$ group has been bound and eliminating the —NH—C(=Y)$NHR_3$ group.

As one example of the above, specifically, a thionoformate group was first introduced into the thiol group of the cysteine residue. And, a peptide chain in which N-acetylguanidido has been added to its C-terminal was obtained by reacting N-acetylguanidine with this thionoformate group in the organic solvent to cause the cleavage of the peptide chain on the N-terminal-side of the cysteine residue. Further, this N-acetylguanidido-added peptide chain was reacted with thiol $R_4$—SH in the buffer solution to convert into the peptide thioester.

The present inventors have also found that the N-acetylguanidido-added peptide chain and the peptide thioester obtained above can be used in the NCL method.

[Chemical formula 1]

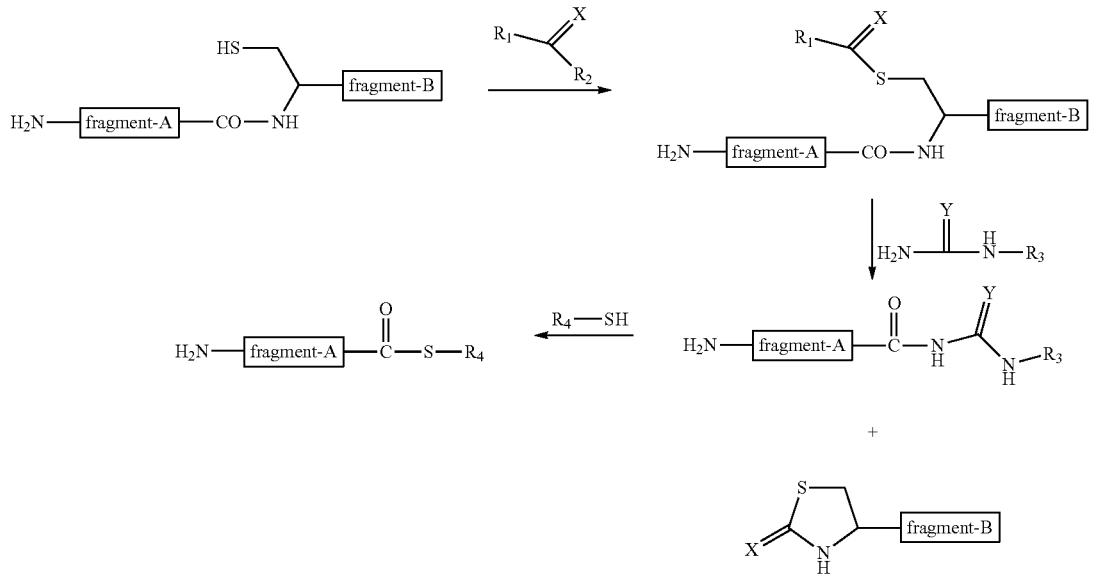

That is, the present invention specifically provides the following [1] to [14].

[1]

A process for producing a peptide thioester, comprising the following steps (a) to (c):

(a) a step of producing a first intermediate by reacting a compound A represented by the following formula (I) with a thiol group of a cysteine residue in a peptide chain having the cysteine residue to eliminate $R_2$:

[Chemical formula 2]

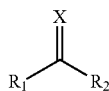

(I)

wherein X is a sulfur atom or an oxygen atom, $R_1$ and $R_2$ are leaving groups;

(b) a step of reacting a compound B represented by the following formula (II) with the first intermediate in an organic solvent to add a —NH—C(=Y)NHR$_3$ group to a carboxyl group forming a peptide bond with an amino acid adjacent to an N-terminal-side of the cysteine residue, and cleaving the peptide bond, thereby obtaining a peptide fragment from the N-terminal-side closer to the N-terminal side than the cleaved peptide bond as a second intermediate:

[Chemical formula 3]

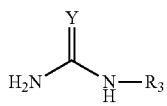

(II)

wherein Y is an oxygen atom, a sulfur atom or an NH group and $R_3$ is a hydrogen atom, an acyl group or an alkoxycarbonyl group; and (c) a step of thioesterifying a C-terminal of the second intermediate by reacting the second intermediate with thiol to exchange the —NH—C(=Y)NHR$_3$ group for the thiol group at the C-terminal.

[2]

The process according to above [1], wherein X is the sulfur atom.

[3]

The process according to above [1] or [2], wherein $R_1$ is a —O—C$_6$ aryl group.

[4]

The process according to any of above [1] to [3], wherein $R_2$ is a halogen atom or a substituted or unsubstituted —S—C$_{6-10}$ aryl group.

[5]

The process according to any of above [1] to [4], wherein Y is an NH group.

[6]

The process according to any of above [1] to [5], wherein $R_3$ is an acetyl group.

[7]

The process according to any of above [1] to [6], wherein the thiol is thiol represented by the following formula (III) in the step (c):

$R_4$—SH    (Formula III)

wherein $R_4$ is any one group selected from a substituted or unsubstituted benzyl group, a substituted or unsubstituted aryl group, and a substituted or unsubstituted alkyl group.

[8]

The process according to any of above [1] to [7], wherein the peptide chain is a recombinant protein.

[9]

The process according to any of above [1] to [8], wherein the peptide chain is a recombinant protein comprising a tag for purification.

[10]

A process for producing a polypeptide comprising a step of binding the peptide thioester obtained by the process according to any of above [1] to [9] to a peptide chain having cysteine at a N-terminal by a ligation method.

[11]

A process for producing a second intermediate used for the process for producing the peptide thioester according to any of [1] to [9] above, comprising:

(a) a step of producing a first intermediate by reacting a compound A represented by the following formula (I) with a thiol group of a cysteine residue in a peptide chain having the cysteine residue to eliminate $R_2$:

[Chemical formula 4]

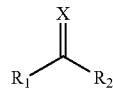

(I)

wherein X is a sulfur atom or an oxygen atom, $R_1$ and $R_2$ are leaving groups; or (b) a step of reacting a compound B represented by the following formula (II) with the first intermediate in an organic solvent to add a —NH—C(=Y)NHR$_3$ group to a carboxyl group forming a peptide bond between the cycteine residue and an amino acid adjacent to an N-terminal-side of the cysteine residue, and cleaving the peptide bond, thereby obtaining a peptide fragment from the N-terminal-side closer to the N-terminal-side than the cleaved peptide bond as a second intermediate:

[Chemical formula 5]

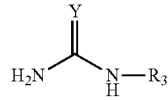

(II)

wherein Y is an oxygen atom, a sulfur atom or an NH group and $R_3$ is a hydrogen atom, an acyl group or an alkoxycarbonyl group.

[12]

A peptide chain having a —NH—C(=Y) NHR$_3$ group at a C-terminal, wherein Y is an oxygen atom or an NH group and $R_3$ is a hydrogen atom, an acyl group or an alkoxycarbonyl group.

[13]

A process for producing a polypeptide comprising a step of binding the peptide chain having the —NH—C(=Y)NHR$_3$ group at the C-terminal according to above [12] to a peptide chain having cysteine at an N-terminal by a ligation method.

[14]

A process for removing a tag for purification added to a C-terminal-side of a recombinant protein, comprising the following steps (a) to (c):

(a) a step of producing a first intermediate by reacting a compound A represented by the following formula (I) with a thiol group of a cysteine residue in the recombinant protein containing the tag for purification on the C-terminal-side to eliminate R$_2$:

[Chemical formula 6]

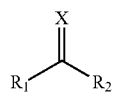

(I)

wherein X is a sulfur atom or an oxygen atom, R$_1$ and R$_2$ are leaving groups;

(b) a step of reacting a compound B represented by the following formula (II) with the first intermediate in an organic solvent to add a —NH—C(=Y)NHR$_3$ group to a carboxyl group forming a peptide bond between the cysteine residue and an amino acid adjacent to an N-terminal-side of the cysteine residue, and cleaving the peptide bond, thereby obtaining a peptide fragment from the N-terminal-side closer to the N-terminal-side than the cleaved peptide bond as a second intermediate:

[Chemical formula 7]

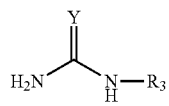

(II)

wherein Y is an oxygen atom, a sulfur atom or an NH group and R$_3$ is a hydrogen atom, an acyl group or an alkoxycarbonyl group; and (c) a step of thioesterifying a C-terminal of the second intermediate by reacting the second intermediate with thiol to exchange the —NH—C(=Y)NHR$_3$ group for the thiol group at the C-terminal.

Effects of the Invention

According to the present invention, a novel process for chemically converting the polypeptide chain into the peptide thioester has been provided.

In the process of the present invention, the peptide chain not having the non-native amino acid derivative, the linker and the particular three-dimensional structure, etc., required for the conventional thioesterification methods can be thioesterified. Therefore, even the long chain polypeptide fragment obtained by the biosynthesis, etc., can be thioesterified easily.

Further, by combining the process of the present invention with the conventional peptide synthesis method, the long chain polypeptide partially having the peptide modification, which was so far difficult to be synthesized can be produced easily and simply by making a fragment of the portion having no modification using the biosynthesis method by which the long chain is relatively easily synthesized, making a fragment of the portion having the modification using the solid-phase synthesis method, and ligating them.

More specifically, the longer sugar chain peptide can be produced easily and simply by chemically synthesizing a fragment alone containing amino acids to which a native binding form of the sugar chain has been added when the modification is performed with the sugar chain, preparing the other portion by biosynthesis and thioesterifying it by the process of the present invention, and ligating them.

The method of subsequently adding the sugar chain and the like to the peptide chain via the linker is also known publicly, and this can also subsequently add the sugar chain to the biosynthesized long chain peptide. However, this sugar chain binding method via the linker binds the sugar chain and the like by utilizing the particular amino acid and its structure. Therefore, for example, when multiple sites capable of binding the sugar chain are present in the peptide, the sugar chain can be added more easily and simply in the site-specific manner compared with the conventional methods, by cutting out a peptide fragment containing the desired binding site alone from a long chain peptide after obtaining the long chain peptide by biosynthesizing, adding the sugar chain thereto, thioesterifying the sugar chain-added peptide fragment using the thioesterification process of the present invention, and ligating again to the remaining portion.

Further, in the biosynthesis, even if the full length protein is normally expressed, its peptide fragment can be wrongly recognized, degraded or not expressed normally in the cell. It is also possible that after synthesizing the full length protein, its fragment alone to be modified is cut out, the necessary treatment such as modification is given thereto, the modified peptide fragment is thioesterified using the process of the present invention, and the thioesterified fragment is again ligated to the remaining portion to yield the desired modified protein.

As described above, the peptide thioesterification process of the present invention is generally useful for synthesis of the proteins.

DETAILED DESCRIPTION OF PREFERRED EMBODIMENTS

Suitable embodiments of the present invention will be described below.

The present invention provides a novel process for producing the peptide thioester, comprising the following steps (a) to (c):

(a) a step of producing a first intermediate by reacting a compound A represented by the following formula (I) with a thiol group of a cysteine residue in a peptide chain having the cysteine residue to eliminate R$_2$:

[Chemical formula 8]

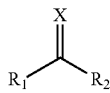

(I)

wherein X is a sulfur atom or an oxygen atom, R$_1$ and R$_2$ are leaving groups;

(b) a step of reacting a compound B represented by the following formula (II) with the first intermediate in an organic solvent to add a —NH—C(=Y)NHR$_3$ group to a carboxyl group forming a peptide bond between the cysteine residue and an amino acid adjacent to an N-terminal-side of the cysteine residue, and cleaving the peptide bond, thereby obtaining a peptide fragment from the N-terminal-side closer to the N-terminal-side than the cleaved peptide bond as a second intermediate:

[Chemical formula 9]

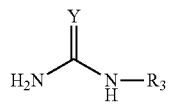

(II)

wherein Y is an oxygen atom, a sulfur atom or an NH group and $R_3$ is a hydrogen atom, an acyl group or an alkoxycarbonyl group; and (c) a step of thioesterifying a C-terminal of the second intermediate by reacting the second intermediate with thiol to exchange the —NH—C(=Y)NHR$_3$ group for the thiol group at the C-terminal.

In the present invention, the "peptide" is not particularly limited as long as two or more amino acids are bound via amide bond(s), and includes publicly known peptides, novel peptides and modified peptides. Those commonly referred to as the protein are included in the peptides in the present invention. Also in the present invention, the "polypeptide" is included in the peptides. The peptide chain used for the process of the present invention may be the native protein or the peptide chain obtained by methods such as the biosynthesis, the chemical synthesis or the cell-free synthesis.

In the present invention, the "modified peptide" includes natural variants of the peptides, post-translational modified peptides, or artificially modified compounds. Such an modification includes, for example, alkylation, acylation (e.g., acetylation), amidation (e.g., amidation of C-terminal of peptide), carboxylation, ester formation, disulfide bond formation, glycosylation, lipidation, phosphorylation, hydroxylation, binding of labeled component, etc., in one or more amino acid residues in the peptide.

In the present invention, the "amino acid" is used in its broadest context, and includes not only native amino acids such as serine (Ser), asparagine (Asn), valine (Val), leucine (Leu), isoleucine (Ile), alanine (Ala), tyrosine (Tyr), glycine (Gly), lysine (Lys), arginine (Arg), histidine (His), aspartic acid (Asp), glutamic acid (Glu), glutamine (Gln), threonine (Thr), cysteine (Cys), methionine (Met), phenylalanine (Phe), tryptophan (Trp) and praline (Pro), but also non-native amino acids such as amino acid variants and derivatives. Those skilled in the art will understand that the amino acids in the present invention include, for example, L-amino acids; D-amino acids, chemically modified amino acids such as amino acid variants and derivatives; amino acids such as norleucine, β-alanine and ornithine that are not constitutive materials for the proteins in vivo; and compounds chemically synthesized to have amino acid properties known to those skilled in the art, etc., in consideration of this broad definition.

In the present invention, the peptide chain to be thioesterified is not particularly limited as long as the peptide chain contains the cysteine residue. For example, an origin, a synthesis method, a size and the like of the peptide chain are not particularly limited. The peptide chain may also have the modification and a protective group.

The number of cysteine residues contained in the peptide chain used in the present invention is not particularly limited, and the peptide chain is cleaved by targeting the cysteine residues. Therefore, it is necessary to design a basic skeleton of the finally synthesized protein depending on the sites having the cysteine residue, and those skilled in the art can easily design such a basic skeleton. The cysteine residues other than the desired cysteine residues may be protected with protective groups in advance so that the thioesterification is performed at positions of only the desired cysteine residues and the remaining cysteine residues are not affected by the reaction in the peptide chain containing the multiple cysteine residues. Examples of such a protective group include an Acm group.

The peptide chain used in the present invention may have a fat-soluble protective group on the N-terminal-side. Preferable protective groups can include, but are not limited to acyl groups such as an acetyl (Ac) group, carbonyl-containing groups such as a t-butyloxycarbonyl (Boc) group, a 9-fluorenylmethoxycarbonyl (Fmoc) group and an allyloxycarbonyl (Alloc) group, and an allyl group and a benzyl group.

The peptide chain used for the process of the present invention may be a native protein or the peptide chain obtained by methods such as the biosynthesis, the chemical synthesis or the cell-free synthesis, and is preferably a recombinant protein expressed in a bacterial cell or a cell. The recombinant protein may be those having the same peptide sequence as in the native protein or those having the peptide sequence having the modification such as a tag for mutation or purification as long as the protein is expressed artificially in the bacterial cell or the cell.

The recombinant protein used in the present invention can be prepared by the method known to those skilled in the art. For example, the recombinant protein can be expressed by introducing an objective gene into a recombinant vector. The recombinant vector used in the present invention may be those capable of transforming a host cell, and a plasmid for *Escherichia coli*, a plasmid for *Bacillus subtilis*, a plasmid for yeast, and animal virus vectors such as retrovirus, vaccinia virus and baculovirus are used. These preferably have a regulatory sequence such as a promoter capable of appropriately expressing the protein in the host cell. Moreover, the host cell may be those capable of expressing a foreign gene in the recombinant vector, and generally *Escherichia coli*, *Bacillus subtilis*, yeast, insect cells and animal cells are used.

The method ordinarily used in general may be used as the method of transfecting the recombinant vector into the host cell. For example, a calcium chloride method and an electroporation method in the case of *Escherichia coli* and a lithium chloride method and the electroporation method in the case of the yeast can be utilized. Transformation of the animal cell can be performed using a physical method such as the electroporation method, a chemical method such as a liposome method and a calcium phosphate method, or a viral vector such as retrovirus. A culture condition of the host cell that is a transformant may be selected in consideration of nutritional and physiological properties of the host cell.

It is preferable that the peptide used in the present invention is purified. The peptide can be purified by an ordinary purification method. For example, in the case of a recombinant protein, a bacterial cell or a cell expressing the recombinant protein used in the present invention is cultured, subsequently the bacterial cell or the cell is collected by a known method, then suspended in an appropriate buffer solution, disrupted by sonication, lysozyme and/or freezing and thawing, and then a crude extract solution of a peptide is prepared by centrifugation or filtration. A protein denaturing agent such as urea and guanidine hydrochloride, and a surfactant such as Triton X-100™ may be contained in the buffer solution. The peptide contained in the extract solution or the culture supernatant obtained as above can be purified by the known purification method. For example, the peptide can be isolated and purified by appropriately selecting and combining affinity chromatography, ion exchange chromatography, filter, ultrafiltration, gel filtration, electrophoresis, salting out, dialysis, and the like.

A tag for the purification can be incorporated into the expression vector in order to make the purification of the recombinant protein easy. Examples of the tag for the purification include, for example, an His tag, a GST tag, a Myc tag, a FLAG tag, and a maltose-binding protein (MBP). In the present invention, the N-terminal-side from Cys arranged within the peptide chain is thioesterified, thus the tag for the purification is added to the C-terminal-side of the peptide and the peptide after the purification is thioesterified, whereby the C-terminal-side from Cys in the peptide chain which includes the tag is cut off and the peptide thioester can be obtained efficiently. By arranging Cys to the desired position on the peptide chain, it is also possible to use the process of the present invention for removal of the tag on the C-terminal-side.

Therefore, the process for removing the tag for the purification added to the C-terminal of the recombinant protein by using the process for producing the peptide thioester of the present invention is also included in the present invention.

In the present invention, the "peptide thioester" (hereinafter sometimes also simply described as the "thioester") refers to the peptide having a carboxythioester moiety (—C=O—SR) at the C-terminal. The peptide thioester used in the present invention is not particularly limited as long as the thioester can cause the exchange reaction with other thiol groups. R group includes for example, groups exemplified in $R_4$ below.

In the process of the present invention, first (a) a step of reacting a compound A with a thiol group of a cysteine residue in a peptide chain having the cysteine residue for producing the first intermediate is performed.

In the present invention, the compound A is represented by the following formula (T).

[Chemical formula 10]

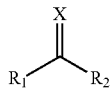

(I)

In the formula, X is a sulfur atom or an oxygen atom, and preferably the sulfur atom.

$R_1$ and $R_2$ are not particularly limited as long as they have lower nucleophilicity than an atom or an atomic group to be substituted and have a function to be eliminated under a reaction condition of the following step (a) as leaving groups, and it is preferable that $R_1$ and $R_2$ are different leaving groups from each other. Examples of $R_1$ and $R_2$ include specifically halogen atoms, substituted or unsubstituted —O-alkyl groups, substituted or unsubstituted —O-alkenyl groups, substituted or unsubstituted —O-alkynyl groups, substituted or unsubstituted —O-aryl groups, substituted or unsubstituted —O-heteroaryl groups, substituted or unsubstituted —S-alkyl groups, substituted or unsubstituted —S-alkenyl groups, substituted or unsubstituted —S-alkynyl groups, substituted or unsubstituted —S-aryl groups, or substituted or unsubstituted —S-heteroaryl groups. More preferably, examples of $R_1$ and $R_2$ include combinations of $R_1$ that is the leaving group selected from the group consisting of substituted or unsubstituted —O—$C_{5-10}$ aryl groups and substituted or unsubstituted —S—$C_{1-8}$ alkyl groups and $R_2$ that is the leaving group selected from the group consisting of halogen atoms, substituted or unsubstituted alkyl groups and substituted or unsubstituted —S—$C_{6-10}$ aryl groups.

In the present invention, the "alkyl group" is a monovalent group derived from aliphatic hydrocarbon by removing any one hydrogen atom, and has a subset of hydrocarbyl or hydrocarbon containing hydrogen and carbon atoms. The alkyl group includes a straight chain or branched chain structure. The alkyl group of the present invention preferably includes the alkyl groups having 1 to 8 carbon atoms. "$C_{1-8}$ alkyl group" indicates the alkyl group having 1 to 8 carbon atoms, and specific examples thereof include methyl, ethyl, propyl, butyl, pentyl, hexyl, heptyl and octyl groups.

In the present invention, the "alkenyl group" is a monovalent group having at least one double bond. Geometrical forms of the double bonds can take Entgegen (E), Zusammen (Z), cis or trans configurations depending on the configuration of the double bonds and substituents. The alkenyl group includes the straight chain or branched chain form. The alkenyl group of the present invention preferably includes the alkenyl groups having 2 to 8 carbon atoms. "$C_{2-8}$ alkenyl group" indicates the alkenyl group having 2 to 8 carbon atoms, and specific examples thereof include vinyl, allyl, propenyl, butenyl, pentenyl, hexenyl, heptenyl and octenyl groups.

In the present invention, the "alkynyl group" is a monovalent group having at least one triple bond. The alkynyl group includes straight chain or branched chain alkynyl groups. The alkynyl group of the present invention preferably includes the alkynyl groups having 2 to 8 carbon atoms. "$C_{2-8}$ alkynyl group" indicates the alkynyl group having 2 to 8 carbon atoms, and specific examples thereof include ethynyl, 1-propynyl, 2-propynyl, butynyl, pentynyl, hexynyl, heptynyl, and octynyl groups.

In the present invention, the "aryl group" means an aromatic hydrocarbon ring group. The aryl group of the present invention preferably includes the aryl groups having 6 to 10 carbon atoms "$C_{6-10}$ aryl group" indicates the aryl group having 6 to 10 carbon atoms, and specific examples thereof include phenyl, 1-naphthyl and 2-naphthyl groups.

In the present invention, the "heteroaryl group" means a monovalent or bivalent group derived from a heteroaryl ring by removing one or two hydrogen atoms at any position(s). In the present invention, the "heteroaryl ring" means an aromatic ring having one or multiple heteroatoms in atoms composing the ring, and is preferably 5 to 9 membered rings. The ring may be a monocyclic or bicyclic heteroaryl group obtained by being fused with a benzene ring or a monocyclic heteroaryl ring. Specific examples thereof include furanyl, thiophenyl, pyrrolyl, benzofuranyl, benzothiophenyl, indolyl, pyridyl, and quinolyl groups.

Types, numbers and substituted positions of substituents that the aforementioned leaving groups have are not particularly limited, and examples of the substituents include alkyl, alkenyl, alkoxy, aryl, formyl, carbonyl, carboxyl, alkylcarboxyl, alkoxycarbonyl, halogen, sulfonyl or nitro groups.

The compound A of the present invention includes more specifically the followings.

[Chemical formula 11]

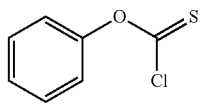

-continued

[Chemical formula 12]

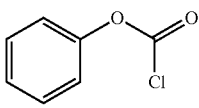

[Chemical formula 13]

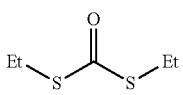

[Chemical formula 14]

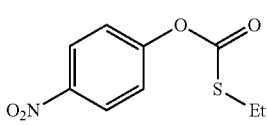

Also, the above-described compound

[Chemical formula 15]

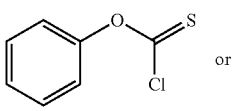 or

[Chemical formula 16]

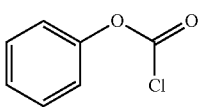

can be reacted with MPAA ((4-carboxymethyl)thiophenol) to produce the following thionoformate reagent, which can also be used:

[Chemical formula 17]

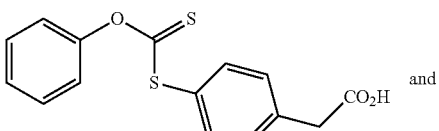 and

[Chemical formula 18]

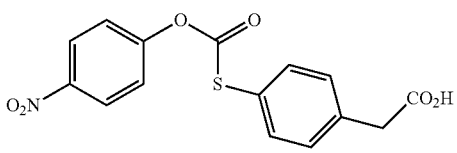

The first intermediate in which the —C(=X)—$R_1$ group is bound to the SH group in the cysteine residue as shown in the following figure can be obtained by reacting the compound A of the present invention with the cysteine residue in the peptide.

[Chemical formula 19]

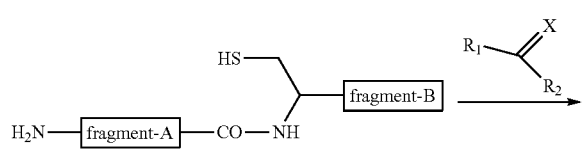

-continued

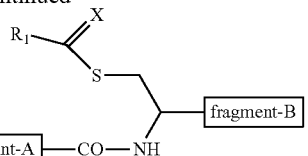

In the present invention, the step (a) is preferably performed under an acidic condition, particularly at pH 3 to 5. The reaction is preferably performed in a mixed solvent of buffer solution and acetonitrile at 0 to 50° C., preferably 15 to 25° C. for about 0.1 to 3 hours, preferably 10 minutes to one hour, but is not limited thereto.

Then, in the present invention, the step (b) is performed, in which the peptide fragment on the N-terminal-side closer to the N-terminal-side than the cleaved peptide bond is obtained as the second intermediate by reacting the compound B with the first intermediate in the organic solvent to add the —NH—C(=Y)$NHR_3$ group to the carboxyl group forming the peptide bond with the amino acid adjacent to the N-terminal-side of the cysteine residue, and cleaving the peptide bond.

In the present invention, the compound B is represented by the following formula (II).

[Chemical formula 20]

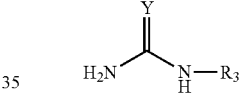

(II)

In the formula, Y is an oxygen atom, an NH group or a sulfur atom, and $R_3$ is a hydrogen atom, an acyl group, or an alkoxycarbonyl group.

In the present invention, the "acyl group" means an atomic group obtained by removing an OH group from a carboxyl group of a carboxylic acid. The acyl group of the present invention preferably includes the acyl groups having 1 to 4 carbon atoms, and specific examples thereof include acetyl, propionyl and butyroyl groups.

In the present invention, the "alkoxy group" means an oxy group bound to the "alkyl group." The alkoxy group of the present invention may be straight chain or branched chain. The alkoxy group of the present invention preferably includes the straight chain alkoxy groups having 1 to 14 carbon atoms and the branched chain alkoxy groups having 3 to 14 carbon atoms. Specifically, for example, methoxy, ethoxy, n-propyloxy, isopropoxy, n-butoxy, 2-methyl-2-propyloxy, n-pentyloxy, and n-hexyloxy groups can be included.

Also, "$C_{2-n}$ alkoxycarbonyl group" means the carbonyl group having a $C_{1-(n-1)}$ alkoxy group. The alkoxycarbonyl group of the present invention preferably includes the alkoxycarbonyl groups having 2 to 15 carbon atoms. Specifically, for example, methoxycarbonyl, ethoxycarbonyl, n-propyloxycarbonyl, isopropoxycarbonyl, n-butoxycarbonyl, 2-methyl-2-propyloxycarbonyl, n-pentyloxycarbonyl, and n-hexyloxycarbonyl groups can be included.

The acyl group preferably includes the acetyl group. Also the alkoxycarbonyl group preferably includes a tert-butoxycarbonyl (Boc) group.

The compound B of the present invention includes more specifically the following.

[Chemical formula 21]

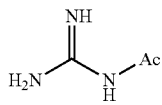

[Chemical formula 22]

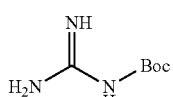

[Chemical formula 23]

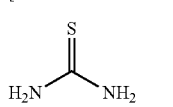

[Chemical formula 24]

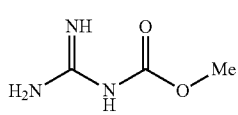

In the present invention, the step (b) is preferably performed in the presence of the organic solvent. It is preferable that the organic solvent is high in solubility and low in nucleophilicity. Such an organic solvent can include, for example, DMSO, DMF and dioxane. The reaction is preferably performed at 0 to 50° C., preferably 15 to 25° C. for about 1 to 24 hours, preferably 5 to 10 hours, but is not limited thereto.

The peptide chain is cleaved on the N-terminal-side of the cysteine residue as shown in the following figure by adding the —NH—C(=Y)NHR$_3$ group to the carboxyl group forming the peptide bond between the cysteine residue and the amino acid adjacent to the N-terminal-side of the cysteine residue.

[Chemical formula 25]

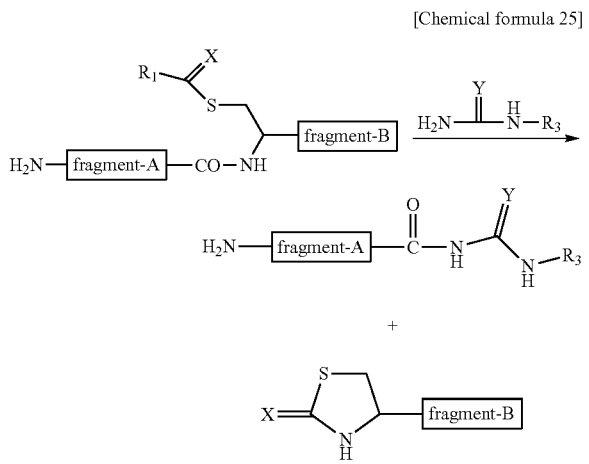

When the peptide has the amino group in its side chain, a fat-soluble protective group may be introduced to the amino group in the side chain before performing the step (b) of the present invention. The fat-soluble protective group can include, but is not limited to, protective groups such as carbonyl-containing groups such as a 9-fluorenylmethoxycarbonyl (Fmoc) group, a t-butyloxycarbonyl (Boc) group and an allyloxycarbonyl (Alloc) group, acyl groups such as an acetyl (Ac) group, and an allyl group and a benzyl group.

In order to introduce the fat-soluble protective group, for example, the Fmoc group can be introduced by adding 9-fluorenylmethyl-N-succinimidyl carbonate and sodium hydrogen carbonate and reacting them. The reaction is preferably performed at 0 to 50° C. preferably at room temperature for about 1 to 5 hours, but is not limited thereto.

The peptide fragment on the N-terminal-side closer to the N-terminal-side than the cleaved site of the cleaved peptide chain can be obtained as the second intermediate by the following formula (I) in the step (b).

[Chemical formula 26]

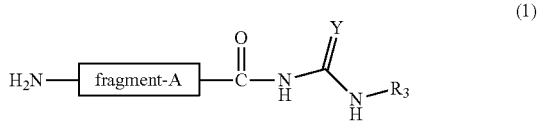

(1)

The process for producing the peptide thioester of the present invention further includes the step (c) of thioesterifying the C-terminal of the second intermediate by reacting thiol with the second intermediate to exchange the —NH—C(=Y)NHR$_3$ group at the C-terminal for the thiol group.

The second intermediate used for the step (c) may be isolated or need not be isolated after the step (b).

In preferable embodiments, thiol represented by the following formula (III):

$R_4$—SH   (Formula III)

is used in the step (c).

$R_4$ is not particularly limited as long as it does not inhibit the thiol exchange reaction and becomes the leaving group in a substitution reaction on carbonyl carbon. Preferably, $R_4$ is any one group selected from substituted or unsubstituted benzyl groups, substituted or unsubstituted aryl groups and substituted or unsubstituted alkyl groups. More preferably, $R_4$ is any one group selected from the substituted or unsubstituted benzyl groups, substituted or unsubstituted $C_{6-10}$ aryl groups and substituted or unsubstituted $C_{1-8}$ alkyl groups. More specifically, $R_4$ can be selected from benzyl type leaving groups such as benzylmercaptan, aryl type leaving groups such as thiophenol and 4-(carboxymethyl)thiophenol, alkyl type leaving groups such as a 2-mercaptoethanesulfonic acid group and 3-mercaptopropionate amide, etc. The type, the number and the substituted position of the substituents that these leaving groups have are not particularly limited.

The second intermediate is completely converted into the thioester as the following figure by performing the step (c).

[Chemical formula 27]

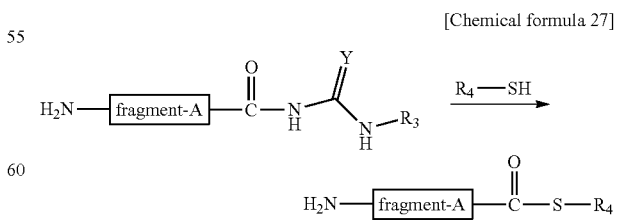

The peptide thioester obtained as in the above can be ligated to a peptide (or a modified peptide) which contains an amino acid residue having the —SH group at the N-terminal among the peptides or the modified peptides by using the ligation method. Therefore, the present invention also provides a process for producing a polypeptide comprising a step of binding the peptide thioester obtained by the process of the present invention to the peptide chain having cysteine at the N-terminal by the ligation method.

It is also possible to use the second intermediate obtained in the step (b) in place of the above peptide thioester for the ligation method.

In the present invention, the "ligation method" includes not only the native chemical ligation method (NCL method) described in Patent Literature 1, but also the cases of applying the native chemical ligation method to the peptides containing the non-native amino acid and amino acid derivative (e.g., threonine derivative A, protected methionine, sugar chain-added amino acids, etc.). The peptide having the native amide bond (peptide bond) at the ligated site can be produced by the ligation method.

The ligation using the ligation method can be performed in any cases of between the peptide and the peptide, between the peptide and the modified peptide, and between the modified peptide and the modified peptide.

The terms used herein are used for describing particular aspects and are not intended to limit the present invention.

The term "comprising" (also, "containing" and "including") used herein intends that the described respects (members, steps, elements and numerals, etc.) are present except the cases to be understood obviously different in context, and it is not excluded that the respects (members, steps, elements and numerals, etc.) other than these are present.

Unless otherwise defined differently, all of the terms (including technical terms and scientific terms) used herein have the same meanings as those understood widely by those skilled in the art to which the present invention belongs. The terms used herein should be construed to have the meanings coherent to the meanings in this specification and the related technical field unless a different definition is otherwise manifested, and should not be construed in idealized or unduly formal meanings.

The aspects of the present invention are sometimes described with reference to the schematic view. When described in the schematic view, the embodiment is sometimes expressed in a exaggerated manner in order to describe it clearly.

The terms such as first and second are used to express various elements, but it is understood that these elements are not to be limited to those terms. These terms are used only for distinguishing one element from the other element, and without departing from the scope of the present invention, it is possible that the first element is written as the second element, as well as the second element is written as the first element.

The present invention will be described in more detail with reference to the following Examples. However, the present invention can be embodied by various aspects, and is not to be construed to be limited to Examples described here.

EXAMPLES

Example 1

Introduction of Thionoformate Group (Synthesis of MPAA Phenyl Thionoformate)

[Chemical formula 28]

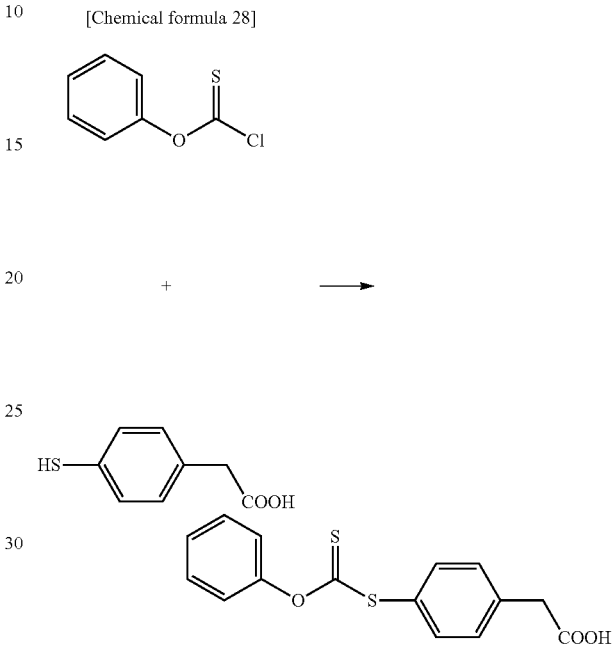

MPAA ((4-carboxymethyl)thiophenol) (98 mg, 0.583 mmol) and phenyl chlorothionoformate (103 μL, 0.76 mmol) were dissolved in dichloromethane (400 μL), and the mixture was stirred at room temperature for one hour. After one hour, the reaction solution was diluted with 2.0 mL of chloroform, 1.0 mL of an aqueous solution of saturated sodium bicarbonate was added, and the mixture was extracted and washed with chloroform. A chloroform layer was washed with saturated saline, dried on magnesium sulfate, and then concentrated under reduced pressure to give a yellow clear residue in a syrup shape. This was then used as a thionoformate reagent (MPAA phenyl thionoformate) (MW: 305.3, MS: no available data).

(Introduction of Thionoformate Group by MPAA Phenyl Thionoformate Reagent)

A peptide (Ac-Val Try Ala Xaa Cys Gly-OH) (SEQ ID NO: 1), Xaa=Lys (SEQ ID NO: 2), Ser (SEQ ID NO: 3), Asp (SEQ ID NO: 4), Ala (SEQ ID NO: 5), Val (SEQ ID NO: 6), crude (mixture of Lys, Ser, Asp, Ala and Val), 6 mg) was dissolved in a buffer solution at pH 5.5 (1.0 mL of 0.2 MNa$_2$HPO$_4$ and 6M Gn-HCl), and then a total amount of MPAA phenyl thionoformate (15 μL) dissolved in acetonitrile (230 μL) was added thereto. After one hour, the reaction solution was washed with Et$_2$O. The purification was performed by HPLC to yield an objective compound. The reaction was quantitatively performed as a result of HPLC.

(Xaa=Lys, ESIMS calcd [M+H]$^+$ 818.3, found [M+H]$^+$ 818.4)

(Xaa=Ser, ESIMS calcd [M+H]$^+$ 777.3, found [M+H]$^+$ 777.3)

(Xaa=Asp, ESIMS calcd [M+H]$^+$ 805.3, found [M+H]$^+$ 805.3)

(Xaa=Ala, ESIMS calcd [M+H]⁺ 761.3, found [M+H]⁺ 761.3)

(Xaa=Val, ESIMS calcd [M+H]⁺ 789.3, found [M+H]⁺ ---)

A peptide (Ac-Val Try Ala Xaa Cys Gly-OH) (SEQ ID NO: 1), Xaa=Ser (SEQ ID NO: 3), Phe (SEQ ID NO: 8), Leu (SEQ ID NO: 7), crude (mixture of Ser, Phe and Leu), 10 mg) was dissolved in the buffer solution at pH 5.0 (2.0 mL of 0.2 M Na$_2$HPO$_4$ and 6 M Gn-HCl) and then MPAA phenyl thionoformate (5 μL) dissolved in acetonitrile (700 μL) was added thereto. After 1.5 hours, the reaction solution was washed with Et$_2$O. The purification was performed by HPLC to yield an objective compound. The reaction was quantitative as a result of HPLC.

(Xaa=Ser, ESIMS calcd [M+H]⁺ 777.3, found [M+H]⁺ 777.3)

(Xaa=Leu, ESIMS calcd [M+H]⁺ 803.4, found [M+H]⁺ 803.3)

(Xaa=Phe, ESIMS calcd [M+H]⁺ 837.4, found [M+H]⁺ 837.3)

The thionoformate group was introduced into the —SH group of cysteine regardless of the type of amino acid adjacent to the N-terminal-side of the cysteine.

Example 2

N-acetylguanidinylation Reaction

[Chemical formula 29]

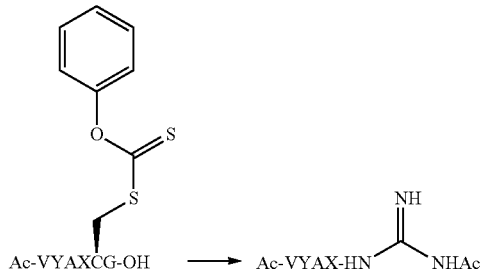

(Performed with Xaa=Ala, Leu, Phe, Ser and Lys)

(Case of Xaa=Ala)

Ac-Val Tyr Ala Ala Cys(C(S)OPh)Gly-OH (SEQ ID NO: 9) (0.2 mg, 0.28 μmol) was dissolved in 250 mM N-acetylguanidine/DMSO solution (260 μL). After two hours, a compound was precipitated with and washed with Et$_2$O. The objective compound was purified by HPLC to yield objective N-acetylguanidido (Ac-Val Tyr Ala Ala-NHC(NH)NHAc (SEQ ID No: 10) (yield: 80%, calculated from HPLC area intensity).

(ESIMS calcd [M+H]⁺ 548.3, found [M+H]⁺ 548.4)

(Case of Xaa=Leu or Phe)

A mixture of Ac-Val Tyr Ala Leu Cys(C(S)OPh)Gly-OH (SEQ ID NO:11) (0.1 mg, 0.12 μmol) and Ac-Val Tyr Ala Phe Cys (C(S)OPh) Gly-OH (SEQ ID NO: 12) (0.1 mg, 0.12 μmol) was dissolved in 250 mM N-acetylguanidine/DMSO solution (100 μL). After 4.5 hours, compounds were precipitated and washed with Et$_2$O. The objective compounds were purified by HPLC to yield objective N-acetylguanidido (Ac-Val Tyr Ala Leu-NHC(NH)NHAc (SEQ ID No: 13) and Ac-Val Tyr Ala Phe-NHC(NH)NHAc (SEQ ID No: 14) (yield: 80%, calculated from HPLC area intensity).

(Xaa=Leu, ESIMS calcd [M+H]⁺ 590.3, found [M+H]⁺ 590.3)

(Xaa=Phe, ESIMS calcd [M+H]⁺ 624.3, found [M+H]⁺ 624.3)

(Case of Xaa=Ser)

Ac-Val Tyr Ala Ser Cys(C(S)OPh)Gly-OH (SEQ ID NO: 15) (0.2 mg, 0.26 μmol) was dissolved in 250 mM N-acetylguanidine/DMSO solution (100 μL). After 3.5 hours, a compound was precipitated with and washed with Et$_2$O. The objective compound was purified by HPLC to yield objective N-acetylguanidido (Ac-Val Tyr Ala Ser-NHC(NH)NHAc (SEQ ID No: 16) (yield: 70%, from HPLC area intensity).

(Case of Xaa=Lys)

A peptide (Ac-Val Tyr Ala Lys Cys (C(S)OPh)Gly-OH (SEQ ID NO: 17) (0.1 mg) was dissolved in DMSO (30 μL) containing Boc$_2$O (0.3 mg) and triethylamine (0.14 μL). After 1.5 hours, the reaction solution was precipitated with and washed with Et$_2$O. The resulting residue was dissolved in 250 mM N-acetylguanidine/DMSO solution (100 μL). After 2.5 hours, the objective compound was purified by HPLC to yield objective N-acetylguanidido (Ac-Val Tyr Ala Lys(Boc)-NHC(NH)NHAc (SEQ ID No: 18) (yield: 70%, calculated from HPLC area intensity).

It was identified that the cysteine residue to which the thionoformate had been added had the reactivity with guanidine to the peptide bond on the N-terminal-side, regardless of the type of amino acid adjacent to the N-terminal-side of the cysteine.

Example 3

Thioesterification of 24 aa Peptide

[Chemical formula 30]

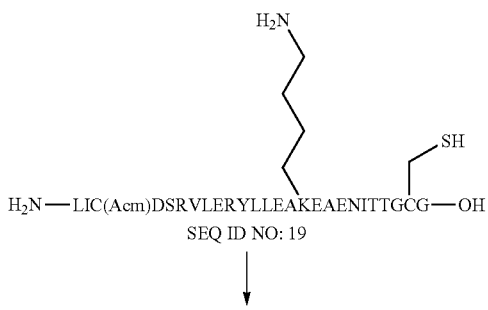

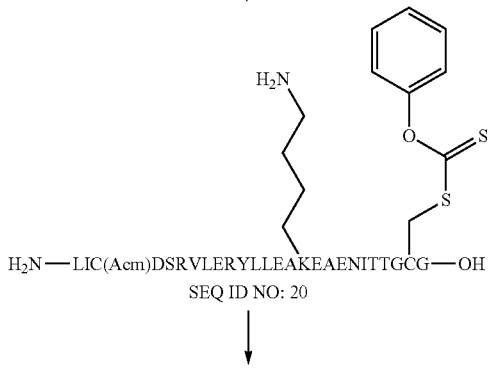

-continued

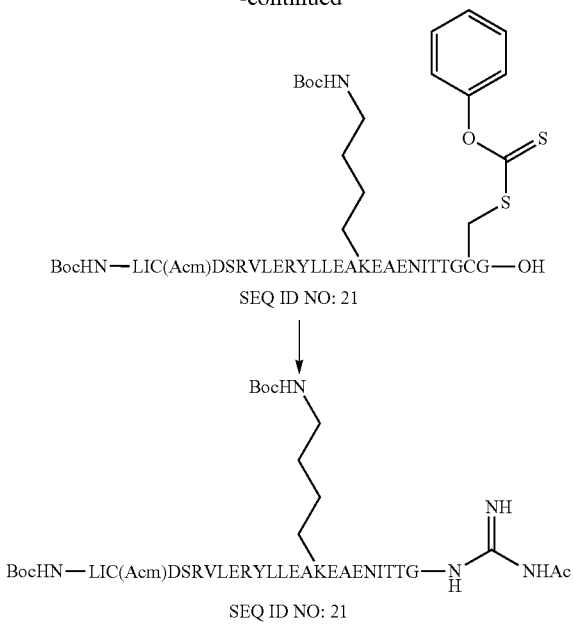

BocHN—LIC(Acm)DSRVLERYLLEAKEAENITTGCG—OH

SEQ ID NO: 21

↓

BocHN—LIC(Acm)DSRVLERYLLEAKEAENITTG—N(H)—C(=NH)—NHAc

SEQ ID NO: 21

A peptide (H$_2$N-Leu Ile Cys(Acm)Asp Ser Arg Val Leu Glu Arg Tyr Leu Leu Glu Ala Lys Glu Ala Glu Asn Ile Thr Thr Gly Cys Gly-OH (SEQ ID NO: 19), crude (not purified)), appropriate amount (estimated about 1 mg) was dissolved in the buffer solution at pH 5.0 (300 μL of 0.2 M Na$_2$HPO$_4$ and 6 M Gn-HCl), and then the total amount of MPAA phenyl thionoformate (1 μL) dissolved in acetonitrile (100 μL) was added thereto. After 50 minutes, the reaction solution was washed with Et$_2$O. The purification was performed by HPLC to yield an objective compound (H$_2$N-Leu Ile Cys(Acm)Asp Ser Arg Val Leu Glu Arg Tyr Leu Leu Glu Ala Lys Glu Ala Gln Asn Ile Thr Thr Gly Cys(C(S)OPh)Gly-OH (SEQ ID NO: 20)). Cys at position 3 was previously protected with Acm not to be affected with the thionoformate reagent.

(ESIMS calcd[M+2H]$^{2+}$1553.8, [M+3H]$^{3+}$ 1035.8, found [M+2H]$^{2+}$ 1552.9, [M+3H]$^{3+}$ 1035.7)

The peptide (H$_2$N-Leu Ile Cys(Acm)Asp Ser Arg Val Leu Gln Arg Tyr Leu Leu Glu Ala Lys Glu Ala Glu Asn Ile Thr Thr Gly Cys(C(S)OPh)Gly-OH (SEQ ID NO: 20), ca. 0.3 mg) was dissolved in DMSO (20 μL) containing Boc$_2$O (0.4 mg) and triethylamine (0.03 μL). After 1.5 hours, the reaction solution was precipitated with and washed with Et$_2$O. The resulting residue was dissolved in 250 mM N-acetylguanidine/DMSO solution (50 μL). After 2.5 hours, the objective compound was purified by HPLC to yield objective N-acetylguanidido (BocHN-Leu Ile Cys(Acm)Asp Ser Arg Val Leu Glu Arg Tyr Leu Leu Glu Ala Lys(Boc)Glu Ala Glu Asn Ile Thr Thr Gly-NHC(NH)NHAc (SEQ ID NO: 21)).

(ESIMS calcd [M+2H]$^{2+}$ 1546.8, [M+3H]$^{3+}$ 1031.5, found [M+2H]$^{2+}$1547.0, [M+3H]$^{3+}$ 1031.4)

The 24 aa peptide (BocHN-Leu Ile Cys(Acm)Asp Ser Arg Val Leu Glu Arg Tyr Leu Leu Glu Ala Lys(Boc)Glu Ala Gln Asn Ile Thr Thr Gly-NHC(NH)NHAc (SEQ ID NO: 21), ca. 0.1 mg>) was dissolved in a buffer solution at pH 7.05 (0.2 M phosphoric acid, 6 M guanidine, 50 μL) containing MESNa (sodium 2-sulfanylethanesulfonate) (1 mg, 2% v/v). After 3.5 hours, the objective compound was purified by HPLC to yield a thioester (BocHN-Leu Ile Cys(Acm)Asp Ser Arg Val Leu Glu Arg Tyr Leu Leu Glu Ala Lys(Boc)Glu Ala Glu Asn Ile Thr Thr Gly-SCH$_2$CH$_2$SO$_3$ (SEQ ID NO: 22)) (unknown yield, about 70% on HPLC).

(ESIMS calcd [M+2H]$^{2+}$ 1567.3, found [M+2H]$^{2+}$ 1566.8)

Example 4

Introduction of Thionoformate Group by Chlorothionoformate Reagent

The peptide (Ac-Val Tyr Ala <u>Ala</u> Cys Gly-OH (SEQ ID NC: 5), 6 mg) was dissolved in the buffer solution at pH 5.0 (961 μL of 0.2 M Na$_2$HPO$_4$ and 6M Gn-HCl), and phenyl chlorothionoformate (6.5 μL) dissolved in acetonitrile (320 μl) was added thereto. After one hour, the reaction solution was washed with Et$_2$O. The purification was performed by HPLC to yield an objective thionoformate-added peptide (SEQ ID NO: 9) (6.4 mg, 88%). (Xaa=Ala, ESIMS calcd [M+H]$^+$ 761.3, found [M+H]$^+$ 761.3)

The peptide (Ac-Val Tyr Ala Leu Cys Gly-OH (SEQ ID NO: 7), 3.4 mg) was dissolved in the buffer solution at pH 5.0 (510 μL of 0.2 μM Na$_2$HPO$_4$ and 6 M Gn-HCl), and phenyl chlorothionoformate (3.5 μl) dissolved in acetonitrile (170 μL) was added thereto. After one hour, the reaction solution was washed with Et$_2$O. The purification was performed by HPLC to yield an objective thionoformate-added peptide (SEQ ID NO: 11) (3.8 mg, 92%). (Xaa=Leu, ESIMS calcd [M+H]$^+$803.4, found [M+H]$^+$803.3)

The peptide (Ac-Val Tyr Ala <u>Phe</u> Cys Gly-OH (SEQ ID NO: 8), 5.1 mg) was dissolved in the buffer solution at pH 5.0 (729 μL of 0.2 M Na$_2$HPO$_4$ and 6M Gn-HCl), and phenyl chlorothionoformate (5.0 μL) dissolved in acetonitrile (243 μl) was added thereto. After one hour, the reaction solution was washed with Et$_2$O. The purification was performed by HPLC to yield an objective thionoformate-added peptide (SEQ ID NO: 12) (5.1 mg, 84%). (Xaa=Phe, ESIMS calcd [M+H]$^+$837.4, found [M+H]$^+$837.3)

The peptide (Ac-Val Tyr Ala <u>Ser</u> Cys Gly-OH (SEQ ID NO: 3), 4.9 mg) was dissolved in the buffer solution at pH 5.0 (766 μL of 0.2 M Na$_2$HPO$_4$ and 6M Gn-HCl), and phenyl chlorothionoformate (5.2 μL) dissolved in acetonitrile (265 μL) was added thereto. After one hour, the reaction solution was washed with Et$_2$O. The purification was performed by HPLC to yield an objective thionoformate-added peptide (SEQ ID NO: 15) (5.5 mg, 92%). (Xaa=Ser, ESIMS calcd [M+H]$^+$ 777.3, found [M+H]$^+$ 777.3)

The peptide (Ac-Val Tyr Ala <u>Lys</u> Cys Gly-OH (SEQ ID NO: 2), 5.5 mg) was dissolved in the buffer solution at pH 5.0 (810 μL of 0.2 M Na$_2$HPO$_4$ and 6M Gn-HCl), and phenyl chlorothionoformate (5.5 μL) dissolved in acetonitrile (270 μL) was added thereto. After one hour, the reaction solution was washed with Et$_2$O. The purification was performed by HPLC to yield an objective thionoformate-added peptide (SEQ ID NO: 17) (6.1 mg, 94%). (Xaa=Lys, ESIMS calcd [M+H]$^+$818.3, found [M+H]$^+$818.4)

Using the chlorothionoformate reagent, the same thionoformate-added peptide chain as that obtained in Example 1 was obtained. Therefore, it has been found that the peptide thioester can also be obtained from the peptide chain in which the thionoformate group was introduced by the chlorothionoformate reagent by performing the N-acetylguanidido addition and then the thioesterification in the same manner as in the peptide chain in which the thionoformate group was introduced in the above Examples 1 and 3.

Industrial Applicability

According to the present invention, a novel process for chemically converting the polypeptide chain into the peptide thioester was provided.

In the process of the present invention, the thioesterification is possible in the peptide chain that does not have the non-native amino acid derivative, the linker or the particular three dimensional structure, etc., required for the conventional thioesterification method, and it is possible to easily thioesterify even in the long chain polypeptide fragment obtained by the biosynthesis, etc. Therefore, the thioesterification process of the present invention can be generally utilized for the synthesis of the proteins.

The invention claimed is:

1. A process for removing a tag for purification added to a C-terminal-side of a recombinant protein, comprising the following steps (a) to (c):
   (a) a step of producing a first intermediate by reacting a compound A represented by the following formula (I) with a thiol group of a cysteine residue to eliminate $R_2$ in a recombinant protein comprising a tag for purification at its C-terminal:

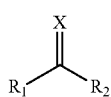　　　(I)

wherein X is a sulfur atom or an oxygen atom, and $R_1$ and $R_2$ are leaving groups;
   (b) step of reacting a compound B represented by the following formula (II) with said first intermediate in an organic solvent to add a —NH—C(=Y)NHR$_3$ group to a carboxyl group forming a peptide bond between the cysteine residue and an amino acid adjacent to an N-terminal-side of said cysteine residue, and cleaving said peptide bond, thereby obtaining a peptide fragment from the N-terminal-side closer to the N-terminal-side than the cleaved peptide bond as a second intermediate:

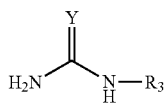　　　(II)

wherein Y is an oxygen atom, a sulfur atom or an NH group and $R_3$ is a hydrogen atom, an acyl group or an alkoxycarbonyl group; and
   (c) a step of thioesterifying a C-terminal of the second intermediate by reacting thiol with the second intermediate to exchange the —NH—C(=Y)NHR$_3$ group at the C-terminal for the thiol group.

2. The process according to claim 1, wherein X is the sulfur atom.

3. The process according to claim 1, wherein $R_1$ is a —O—C$_6$ aryl group.

4. The process according to claim 2, wherein $R_1$ is a —O—C$_6$ aryl group.

5. The process according to claim 1, wherein $R_2$ is a halogen atom, or a substituted or unsubstituted —S—C$_{6\text{-}10}$ aryl group.

6. The process according to claim 2, wherein $R_2$ is a halogen atom, or a substituted or unsubstituted —S—C$_{6\text{-}10}$ aryl group.

7. The process according to claim 3, wherein $R_2$ is a halogen atom, or a substituted or unsubstituted —S—C$_{6\text{-}10}$ aryl group.

8. The process according to claim 1, wherein Y is an NH group.

9. The process according to claim 2, wherein Y is an NH group.

10. The process according to claim 3, wherein Y is an NH group.

11. The process according to claim 5, wherein Y is an NH group.

12. The process according to claim 1, wherein $R_3$ is an acetyl group.

13. The process according to claim 2, wherein $R_3$ is an acetyl group.

14. The process according to claim 3, wherein $R_3$ is an acetyl group.

15. The process according to claim 5, wherein $R_3$ is an acetyl group.

16. The process according to claim 8, wherein $R_3$ is an acetyl group.

17. The process according to claim 1, wherein the thiol in the step (c) is thiol represented by the following formula (III):

$$R_4\text{—SH} \qquad \text{(Formula III)}$$

wherein $R_4$ is any one selected from a substituted or unsubstituted benzyl group, a substituted or unsubstituted aryl group, and a substituted or unsubstituted alkyl group.

18. The process according to claim 2, wherein the thiol in the step (c) is thiol represented by the following formula (III):

$$R_4\text{—SH} \qquad \text{(Formula III)}$$

wherein $R_4$ is any one selected from a substituted or unsubstituted benzyl group, a substituted or unsubstituted aryl group, and a substituted or unsubstituted alkyl group.

19. The process according to claim 3, wherein the thiol in the step (c) is thiol represented by the following formula (III):

$$R_4\text{—SH} \qquad \text{(Formula III)}$$

wherein $R_4$ is any one selected from a substituted or unsubstituted benzyl group, a substituted or unsubstituted aryl group, and a substituted or unsubstituted alkyl group.

20. The process according to claim 5, wherein the thiol in the step (c) is thiol represented by the following formula (III):

$$R_4\text{—SH} \qquad \text{(Formula III)}$$

wherein $R_4$ is any one selected from a substituted or unsubstituted benzyl group, a substituted or unsubstituted aryl group, and a substituted or unsubstituted alkyl group.

* * * * *

```
                          SEQUENCE LISTING

<160> NUMBER OF SEQ ID NOS: 22

<210> SEQ ID NO 1
<211> LENGTH: 6
<212> TYPE: PRT
<213> ORGANISM: Artificial
<220> FEATURE:
<223> OTHER INFORMATION: An artificially synthesized peptide sequence
<220> FEATURE:
<221> NAME/KEY: MISC_FEATURE
<222> LOCATION: (1)..(1)
<223> OTHER INFORMATION: Val having acetyl group
<220> FEATURE:
<221> NAME/KEY: MISC_FEATURE
<222> LOCATION: (4)..(4)
<223> OTHER INFORMATION: Xaa is Lys, Ser, Asp, Ala, Val, Leu or Phe

<400> SEQUENCE: 1

Val Tyr Ala Xaa Cys Gly
1               5

<210> SEQ ID NO 2
<211> LENGTH: 6
<212> TYPE: PRT
<213> ORGANISM: Artificial
<220> FEATURE:
<223> OTHER INFORMATION: An artificially synthesized peptide sequence
<220> FEATURE:
<221> NAME/KEY: MISC_FEATURE
<222> LOCATION: (1)..(1)
<223> OTHER INFORMATION: Val having acetyl group

<400> SEQUENCE: 2

Val Tyr Ala Lys Cys Gly
1               5

<210> SEQ ID NO 3
<211> LENGTH: 6
<212> TYPE: PRT
<213> ORGANISM: Artificial
<220> FEATURE:
<223> OTHER INFORMATION: An artificially synthesized peptide sequence
<220> FEATURE:
<221> NAME/KEY: MISC_FEATURE
<222> LOCATION: (1)..(1)
<223> OTHER INFORMATION: Val having acetyl group

<400> SEQUENCE: 3

Val Tyr Ala Ser Cys Gly
1               5

<210> SEQ ID NO 4
<211> LENGTH: 6
<212> TYPE: PRT
<213> ORGANISM: Artificial
<220> FEATURE:
<223> OTHER INFORMATION: An artificially synthesized peptide sequence
<220> FEATURE:
<221> NAME/KEY: MISC_FEATURE
<222> LOCATION: (1)..(1)
<223> OTHER INFORMATION: Val having acetyl group

<400> SEQUENCE: 4

Val Tyr Ala Asp Cys Gly
```

```
<210> SEQ ID NO 5
<211> LENGTH: 6
<212> TYPE: PRT
<213> ORGANISM: Artificial
<220> FEATURE:
<223> OTHER INFORMATION: An artificially synthesized peptide sequence
<220> FEATURE:
<221> NAME/KEY: MISC_FEATURE
<222> LOCATION: (1)..(1)
<223> OTHER INFORMATION: Val having acetyl group

<400> SEQUENCE: 5

Val Tyr Ala Ala Cys Gly
1               5

<210> SEQ ID NO 6
<211> LENGTH: 6
<212> TYPE: PRT
<213> ORGANISM: Artificial
<220> FEATURE:
<223> OTHER INFORMATION: An artificially synthesized peptide sequence
<220> FEATURE:
<221> NAME/KEY: MISC_FEATURE
<222> LOCATION: (1)..(1)
<223> OTHER INFORMATION: Val having acetyl group

<400> SEQUENCE: 6

Val Tyr Ala Val Cys Gly
1               5

<210> SEQ ID NO 7
<211> LENGTH: 6
<212> TYPE: PRT
<213> ORGANISM: Artificial
<220> FEATURE:
<223> OTHER INFORMATION: An artificially synthesized peptide sequence
<220> FEATURE:
<221> NAME/KEY: MISC_FEATURE
<222> LOCATION: (1)..(1)
<223> OTHER INFORMATION: Val having acetyl group

<400> SEQUENCE: 7

Val Tyr Ala Leu Cys Gly
1               5

<210> SEQ ID NO 8
<211> LENGTH: 6
<212> TYPE: PRT
<213> ORGANISM: Artificial
<220> FEATURE:
<223> OTHER INFORMATION: An artificially synthesized peptide sequence
<220> FEATURE:
<221> NAME/KEY: MISC_FEATURE
<222> LOCATION: (1)..(1)
<223> OTHER INFORMATION: Val having acetyl group

<400> SEQUENCE: 8

Val Tyr Ala Phe Cys Gly
1               5

<210> SEQ ID NO 9
<211> LENGTH: 6
<212> TYPE: PRT
<213> ORGANISM: Artificial
<220> FEATURE:
<223> OTHER INFORMATION: An artificially synthesized peptide sequence
<220> FEATURE:
<221> NAME/KEY: MISC_FEATURE
```

```
<222> LOCATION: (1)..(1)
<223> OTHER INFORMATION: Val having acetyl group
<220> FEATURE:
<221> NAME/KEY: MOD_RES
<222> LOCATION: (5)..(5)
<223> OTHER INFORMATION: Cys having Phenylthionoformate group

<400> SEQUENCE: 9

Val Tyr Ala Ala Cys Gly
1               5

<210> SEQ ID NO 10
<211> LENGTH: 4
<212> TYPE: PRT
<213> ORGANISM: Artificial
<220> FEATURE:
<223> OTHER INFORMATION: An artificially synthesized peptide sequence
<220> FEATURE:
<221> NAME/KEY: MISC_FEATURE
<222> LOCATION: (1)..(1)
<223> OTHER INFORMATION: Val having acetyl group
<220> FEATURE:
<221> NAME/KEY: MOD_RES
<222> LOCATION: (4)..(4)
<223> OTHER INFORMATION: Ala having acetyl guanidido group

<400> SEQUENCE: 10

Val Tyr Ala Ala
1

<210> SEQ ID NO 11
<211> LENGTH: 6
<212> TYPE: PRT
<213> ORGANISM: Artificial
<220> FEATURE:
<223> OTHER INFORMATION: An artificially synthesized peptide sequence
<220> FEATURE:
<221> NAME/KEY: MISC_FEATURE
<222> LOCATION: (1)..(1)
<223> OTHER INFORMATION: Val having acetyl group
<220> FEATURE:
<221> NAME/KEY: MOD_RES
<222> LOCATION: (5)..(5)
<223> OTHER INFORMATION: Cys having Phenylthionoformate group

<400> SEQUENCE: 11

Val Tyr Ala Leu Cys Gly
1               5

<210> SEQ ID NO 12
<211> LENGTH: 6
<212> TYPE: PRT
<213> ORGANISM: Artificial
<220> FEATURE:
<223> OTHER INFORMATION: An artificially synthesized peptide sequence
<220> FEATURE:
<221> NAME/KEY: MISC_FEATURE
<222> LOCATION: (1)..(1)
<223> OTHER INFORMATION: Val having acetyl group
<220> FEATURE:
<221> NAME/KEY: MOD_RES
<222> LOCATION: (5)..(5)
<223> OTHER INFORMATION: Cys having Phenylthionoformate group

<400> SEQUENCE: 12

Val Tyr Ala Phe Cys Gly
1               5

<210> SEQ ID NO 13
<211> LENGTH: 4
<212> TYPE: PRT
```

```
<213> ORGANISM: Artificial
<220> FEATURE:
<223> OTHER INFORMATION: An artificially synthesized peptide sequence
<220> FEATURE:
<221> NAME/KEY: MISC_FEATURE
<222> LOCATION: (1)..(1)
<223> OTHER INFORMATION: Val having acetyl group
<220> FEATURE:
<221> NAME/KEY: MOD_RES
<222> LOCATION: (4)..(4)
<223> OTHER INFORMATION: Leu having acetyl guanidido group

<400> SEQUENCE: 13

Val Tyr Ala Leu
1

<210> SEQ ID NO 14
<211> LENGTH: 4
<212> TYPE: PRT
<213> ORGANISM: Artificial
<220> FEATURE:
<223> OTHER INFORMATION: An artificially synthesized peptide sequence
<220> FEATURE:
<221> NAME/KEY: MISC_FEATURE
<222> LOCATION: (1)..(1)
<223> OTHER INFORMATION: Val having acetyl group
<220> FEATURE:
<221> NAME/KEY: MOD_RES
<222> LOCATION: (4)..(4)
<223> OTHER INFORMATION: Phe having acetyl guanidido group

<400> SEQUENCE: 14

Val Tyr Ala Phe
1

<210> SEQ ID NO 15
<211> LENGTH: 6
<212> TYPE: PRT
<213> ORGANISM: Artificial
<220> FEATURE:
<223> OTHER INFORMATION: An artificially synthesized peptide sequence
<220> FEATURE:
<221> NAME/KEY: MISC_FEATURE
<222> LOCATION: (1)..(1)
<223> OTHER INFORMATION: Val having acetyl group
<220> FEATURE:
<221> NAME/KEY: MOD_RES
<222> LOCATION: (5)..(5)
<223> OTHER INFORMATION: Cys having Phenylthionoformate group

<400> SEQUENCE: 15

Val Tyr Ala Ser Cys Gly
1               5

<210> SEQ ID NO 16
<211> LENGTH: 4
<212> TYPE: PRT
<213> ORGANISM: Artificial
<220> FEATURE:
<223> OTHER INFORMATION: An artificially synthesized peptide sequence
<220> FEATURE:
<221> NAME/KEY: MISC_FEATURE
<222> LOCATION: (1)..(1)
<223> OTHER INFORMATION: Val having acetyl group
<220> FEATURE:
<221> NAME/KEY: MOD_RES
<222> LOCATION: (4)..(4)
<223> OTHER INFORMATION: Ser having acetyl guanidido group

<400> SEQUENCE: 16

Val Tyr Ala Ser
1
```

```
<210> SEQ ID NO 17
<211> LENGTH: 6
<212> TYPE: PRT
<213> ORGANISM: Artificial
<220> FEATURE:
<223> OTHER INFORMATION: An artificially synthesized peptide sequence
<220> FEATURE:
<221> NAME/KEY: MISC_FEATURE
<222> LOCATION: (1)..(1)
<223> OTHER INFORMATION: Val having acetyl group
<220> FEATURE:
<221> NAME/KEY: MOD_RES
<222> LOCATION: (5)..(5)
<223> OTHER INFORMATION: Cys having phenylthionoformate group

<400> SEQUENCE: 17

Val Tyr Ala Lys Cys Gly
1               5

<210> SEQ ID NO 18
<211> LENGTH: 4
<212> TYPE: PRT
<213> ORGANISM: Artificial
<220> FEATURE:
<223> OTHER INFORMATION: An artificially synthesized peptide sequence
<220> FEATURE:
<221> NAME/KEY: MISC_FEATURE
<222> LOCATION: (1)..(1)
<223> OTHER INFORMATION: Val having acetyl group
<220> FEATURE:
<221> NAME/KEY: MOD_RES
<222> LOCATION: (4)..(4)
<223> OTHER INFORMATION: Lys having acetyl guanidido group
<220> FEATURE:
<221> NAME/KEY: MOD_RES
<222> LOCATION: (4)..(4)
<223> OTHER INFORMATION: Lys having blocking group Boc

<400> SEQUENCE: 18

Val Tyr Ala Lys
1

<210> SEQ ID NO 19
<211> LENGTH: 26
<212> TYPE: PRT
<213> ORGANISM: Artificial
<220> FEATURE:
<223> OTHER INFORMATION: An artificially synthesized peptide sequence
<220> FEATURE:
<221> NAME/KEY: MOD_RES
<222> LOCATION: (3)..(3)
<223> OTHER INFORMATION: Cys having blocking group Acm

<400> SEQUENCE: 19

Leu Ile Cys Asp Ser Arg Val Leu Glu Arg Tyr Leu Leu Glu Ala Lys
1               5                   10                  15

Glu Ala Glu Asn Ile Thr Thr Gly Cys Gly
            20                  25

<210> SEQ ID NO 20
<211> LENGTH: 26
<212> TYPE: PRT
<213> ORGANISM: Artificial
<220> FEATURE:
<223> OTHER INFORMATION: An artificially synthesized peptide sequence
<220> FEATURE:
<221> NAME/KEY: MOD_RES
<222> LOCATION: (3)..(3)
<223> OTHER INFORMATION: Cys having blocking group Acm
<220> FEATURE:
```

```
<221> NAME/KEY: MOD_RES
<222> LOCATION: (25)..(25)
<223> OTHER INFORMATION: Cys having Phenylthionoformate group

<400> SEQUENCE: 20

Leu Ile Cys Asp Ser Arg Val Leu Glu Arg Tyr Leu Leu Glu Ala Lys
1               5                   10                  15

Glu Ala Glu Asn Ile Thr Thr Gly Cys Gly
            20                  25

<210> SEQ ID NO 21
<211> LENGTH: 24
<212> TYPE: PRT
<213> ORGANISM: Artificial
<220> FEATURE:
<223> OTHER INFORMATION: An artificially synthesized peptide sequence
<220> FEATURE:
<221> NAME/KEY: MOD_RES
<222> LOCATION: (1)..(1)
<223> OTHER INFORMATION: Leu having blocking group Boc
<220> FEATURE:
<221> NAME/KEY: MOD_RES
<222> LOCATION: (3)..(3)
<223> OTHER INFORMATION: Cys having blocking group Acm
<220> FEATURE:
<221> NAME/KEY: MOD_RES
<222> LOCATION: (16)..(16)
<223> OTHER INFORMATION: Lys having blocking group Boc
<220> FEATURE:
<221> NAME/KEY: MOD_RES
<222> LOCATION: (24)..(24)
<223> OTHER INFORMATION: Gly having acetyl guanidido group

<400> SEQUENCE: 21

Leu Ile Cys Asp Ser Arg Val Leu Glu Arg Tyr Leu Leu Glu Ala Lys
1               5                   10                  15

Glu Ala Glu Asn Ile Thr Thr Gly
            20

<210> SEQ ID NO 22
<211> LENGTH: 24
<212> TYPE: PRT
<213> ORGANISM: Artificial
<220> FEATURE:
<223> OTHER INFORMATION: An artificially synthesized peptide sequence
<220> FEATURE:
<221> NAME/KEY: MOD_RES
<222> LOCATION: (1)..(1)
<223> OTHER INFORMATION: Leu having blocking group Boc
<220> FEATURE:
<221> NAME/KEY: MOD_RES
<222> LOCATION: (3)..(3)
<223> OTHER INFORMATION: Cys having blocking group Acm
<220> FEATURE:
<221> NAME/KEY: MOD_RES
<222> LOCATION: (16)..(16)
<223> OTHER INFORMATION: Lys having blocking group Boc
<220> FEATURE:
<221> NAME/KEY: MOD_RES
<222> LOCATION: (24)..(24)
<223> OTHER INFORMATION: Gly having thioester group

<400> SEQUENCE: 22

Leu Ile Cys Asp Ser Arg Val Leu Glu Arg Tyr Leu Leu Glu Ala Lys
1               5                   10                  15

Glu Ala Glu Asn Ile Thr Thr Gly
            20
```